United States Patent
Labruzzo

(10) Patent No.: US 9,193,673 B2
(45) Date of Patent: Nov. 24, 2015

(54) DERIVATIVES OF MESALAZINE, PROCESS OF THEIR PREPARATION AND THEIR USE IN THE TREATMENT OF INTESTINAL INFLAMMATORY DISEASES

(71) Applicant: Carla Labruzzo, Milan (IT)

(72) Inventor: Carla Labruzzo, Milan (IT)

(73) Assignee: SOFAR SPA, Trezzano Rosa (MI) (IT)

( * ) Notice: Subject to any disclaimer, the term of this patent is extended or adjusted under 35 U.S.C. 154(b) by 373 days.

(21) Appl. No.: 13/683,101

(22) Filed: Nov. 21, 2012

(65) Prior Publication Data

US 2013/0079399 A1 Mar. 28, 2013

Related U.S. Application Data

(63) Continuation-in-part of application No. PCT/IB2011/052175, filed on May 18, 2011.

(30) Foreign Application Priority Data

May 24, 2010 (IT) .............................. MI2010A0929

(51) Int. Cl.
*A61K 31/27* (2006.01)
*A61K 31/225* (2006.01)
*C07C 271/26* (2006.01)
*C07C 229/64* (2006.01)
*C07C 205/60* (2006.01)
*C07C 271/28* (2006.01)

(52) U.S. Cl.
CPC ............. *C07C 229/64* (2013.01); *C07C 205/60* (2013.01); *C07C 271/28* (2013.01)

(58) Field of Classification Search
CPC ............................ C07C 229/64; C07C 271/28
See application file for complete search history.

(56) References Cited

U.S. PATENT DOCUMENTS

2006/0270635 A1 11/2006 Wallace et al.

OTHER PUBLICATIONS

Pellicciari et al, Journal of Medicinal Chemistry, Brush-Border-Enzyme-Mediated Intestine-Specific Drug Delivery. Amino Acid Prodrugs of 5-Aminosalicylic Acid, 1993, .36(26), pp. 4021-4027.*
Roediger et al, Biochemical Pharmacology, Effect of 5-Aminosalicylic Acid (5-ASA) and Other Salicylates on Shortchain Fat Metabolism in the Colonic Mucosa, 1986, 35(2), pp. 221-225.*
Tee, O.S. et al., "Multiple Behaviors in the Cleavage of Aryl Alkanoates by Alfa- and Beta-Cyclodextrins, Process Involving Two Molecules of Cyclodextrins," Journal of the American Chemical Society, vol. 114, 1992, pp. 620-627, XP002616146.
Kurono, Y. et al., "Esterase-Like Activity of Human Serum Albumin, IV. Reactions With Substituted Aspirins and 5-Nitrosalicyl Esters," Chemical and Pharmaceutical Bulletin, vol. 32, 1984, pp. 3715-3719, XP002616147.
Roediger, W. et al., "Effect of 5-Aminosalicylic Acid (5-ASA) and Other Salicylates on Short-Chain Fat Metabolism in the Colonic Mucosa," Biochemical Pharmacology, vol. 35, 1986, pp. 221-225, XP002616148.
PCT International Search Report, International Application No. PCT/IB2011/052175, Filing date: May 18, 2011, Earliest Priority Date: May 24, 2010, Applicant: Sofar SPA, 8 pages.
Italian Search Report, I0 16913, IT MI20100929, The Hague, Date of Completion: Jan. 13, 2011, 8 pages.
Regueiro M., et al., "Clinical Guidelines for the Medical Management of Left-Sided Ulcerative Colitis and Ulcerative Proctitis: Summary Statement," Inflammatory Bowel Disease, Oct. 2006, vol. 12, No. 10, pp. 972-978, Treatment Guidelines: Left-Sided Ulcerative Proctitis, copyright 2006 Lippincott Williams & Wilkins.
Kornbluth, A. et al., "Ulcerative Colitis Practice Guidelines in Adults: American College of Gastroenterology, Practice Parameters Committee," ACG Practice Guidelines, The American Journal of Gastroenterology, vol. 105, Mar. 2010, pp. 501-523, copyright 2010 by the American College of Gastroenterology.
Greene and Wuts, Protective Groups in Organic Synthesis, Third Edition, John Wiley & Sons, Inc., New York, 1999, "Protection for the Amino Group," pp. 503-648.

* cited by examiner

*Primary Examiner* — Paul A Zucker
(74) *Attorney, Agent, or Firm* — Rothwell, Figg, Ernst & Manbeck P.C.

(57) ABSTRACT

The present invention refers to the compounds corresponding to the following general formulas (I) and (Ia):

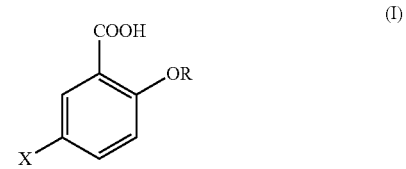

(I)

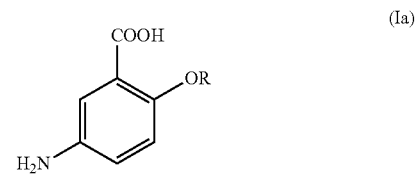

(Ia)

wherein:
R=$C_4$-$C_8$ alkanoyl; and
X=NH—$R_1$ where $R_1$=H, or an amine protecting group;
and/or the pharmaceutically acceptable salts thereof. A further object of the present invention is represented by the use of the compounds of formula (Ia), in particular 5-amino-2-(butyryloxy)benzoic acid and/or pharmaceutically acceptable salts thereof, as a medicament and by the use thereof for the treatment of intestinal inflammatory diseases.

58 Claims, 10 Drawing Sheets

DERIVATIVES OF MESALAZINE, PROCESS OF THEIR PREPARATION AND THEIR USE IN THE TREATMENT OF INTESTINAL INFLAMMATORY DISEASES

CROSS-REFERENCE TO RELATED APPLICATIONS

The present application is a continuation-in-part of International Patent Application No. PCT/IB2011/052175 filed on 18 May 2011 which in turn claims priority to Italian Patent Application No. MI2010A000929 filed on 24 May 2010. Each of these applications is incorporated herein in its entirety.

DESCRIPTION OF THE INVENTION

The present invention refers to the compounds corresponding to the following general formula (I):

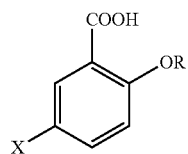

(I)

wherein:
R=$C_4$-$C_8$ alkanoyl; and
X=NH—$R_1$
where $R_1$=H, or protecting group for amines;
and/or the pharmaceutically acceptable salts thereof.

Preferred compounds according to the present invention are represented by the following formula (Ia):

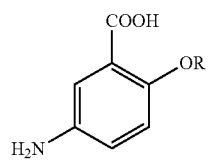

(Ia)

wherein:
R=$C_4$-$C_8$ alkanoyl;
and/or the pharmaceutically acceptable salts thereof.

In a preferred embodiment, an object of the present invention is to provide 5-amino-2-(butyryloxy)benzoic acid and/or the pharmaceutically acceptable salts thereof, preferably hydrochloride salt.

A further object of the present invention is represented by the use of the compounds of formula (Ia), in particular 5-amino-2-(butyryloxy)benzoic acid and/or pharmaceutically acceptable salts thereof, as a medicament and by the use thereof for the treatment of intestinal inflammatory diseases.

The present invention also regards the synthesis processes to obtain such compounds and some intermediate compounds of said synthesis processes.

STATE OF THE ART 5-aminosalicylic acid (hereinafter also referred to as 5-ASA or mesalazine) represents one of the fundamental and historically used drugs in the therapy of both acute and chronic intestinal inflammatory diseases. Actually, it is preferably used for the treatment of IBD, ulcerative colitis, Crohn's disease and IBS. (Regueiro et al. Clinical Guidelines for the Medical Management of left-side ulcerative colitis and ulcerative proctitis: summary statement; Kornbluth A et al. Ulcerative colitis practice guidelines in adults: American college of gastroenterology, practice parameters committee). Such active ingredient has a topical anti-inflammatory action at the intestinal lumen level, with consequent inhibition of biosynthesis of the chemical mediators of the inflammatory process, derivatives of arachidonic acid such as prostaglandin E2, thromboxane B2 and leukotrienes.

Mesalazine does not react systemically but only topically at contact with the mucosa of the lower intestine, distal ileum and colon, selective sites of acute and chronic idiopathic flogosis. Administered orally, mesalazine should thus reach the sites of the disease through tablets or granulates with modified release, a formulation which goes through the stomach and the small intestine unaltered, releasing the active ingredient solely in the distal ileum and, above all, in the colon. Mesalazine is administered rectally preferably in aqueous suspension in form of retention enema, or in suppositories, rectal foam and anorectal gel.

Short Chain Fatty Acids (SCFA) are used for treating intestinal inflammatory diseases. They are used in topical formulations, especially in patients with rectal ulcerative colitis, and in oral formulations, in association with conventional therapy. This family of fatty acids, which comprises acetic acid, propionic acid, isobutyric acid, butyric acid, isovaleric acid, valeric acid, caproic acid, lactic acid and succinic acid is considered the main source of energy for the cells of the colon mucosa and a fundamental factor for controlling the growth of the mucosa.

The food sources of short chain fatty acids are quite limited; they are produced especially during the fermentation of fibres carried out by the bacteria found in the colon. In particular, among these short chain fatty acids, butyric acid represents the largest source of energy for colonocytes to a point that deficiency thereof determines atrophy of the mucosa. In addition, it seems to have positive effects in the prevention of colon cancer given that in vitro, it has proven not only the capacity to inhibit the proliferation of carcinogenic cells but also to stimulate differentiation thereof.

Furthermore, short chain fatty acids perform an anti-inflammatory role on the colon mucosa.

Also regarding butyric acid and derivatives, which perform therapeutic activity thereof locally in acute or chronic intestinal diseases, there arises the need of oral administration through modified release tablets or in form of enema as specified above regarding mesalazine.

Moreover, chronic diseases contrary to acute conditions which can have a rapid onset and/or a short course, are persistent or long-lasting diseases.

A chronic condition is also further distinguished from a recurrent course; recurrent diseases relapse rapidly, with periods of remission or prolonged absence of symptoms in between. Patients suffering from such a condition thus experience alternating periods of active disease and periods of remission.

It is therefore desirable to provide compounds which are efficient either in the active phase of the disease or in the remission phase so as to avoid the reacutization of the disease.

Novel derivatives of mesalazine which are particularly advantageous in the cure of both acute and chronic intestinal inflammatory diseases have now been discovered; in particular, a novel compound capable of combining the therapeutic effects of mesalazine and butyric acid, i.e. 5-amino-2-(butyryloxy)benzoic acid and/or the pharmaceutically acceptable salts thereof, such as hydrochloride have been surprisingly discovered.

DETAILED DESCRIPTION OF THE INVENTION

Figure 1:
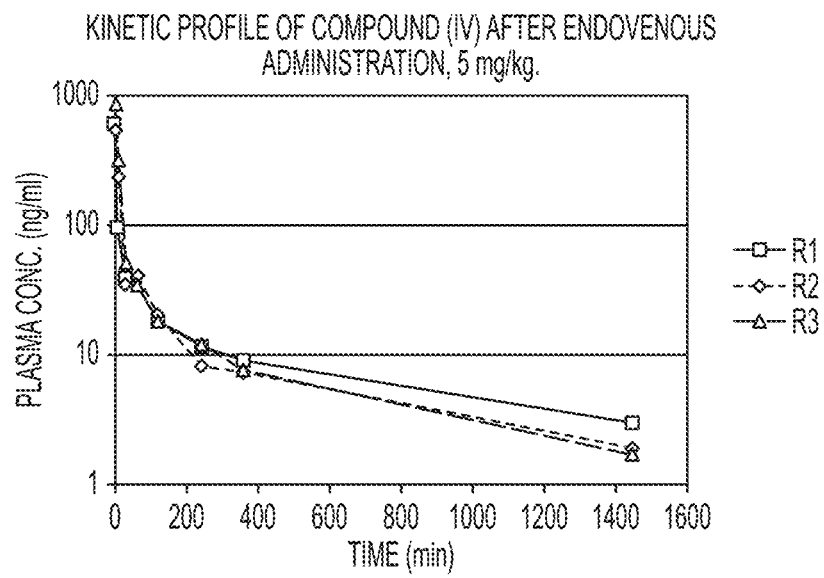
FIG. 1. Kinetic profile of the 5-ASA butyrate after i.v. administration, 5 mg/kg.
Figure 2:
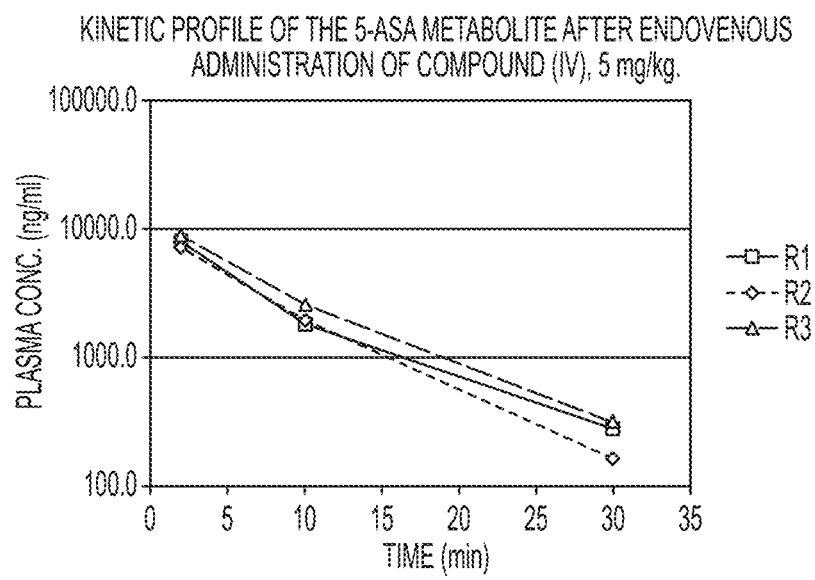
FIG. 2. Kinetic profile of the metabolite 5-ASA after p.o. administration of the 5-ASA butyrate, 50 mg/kg.
Figure 3:
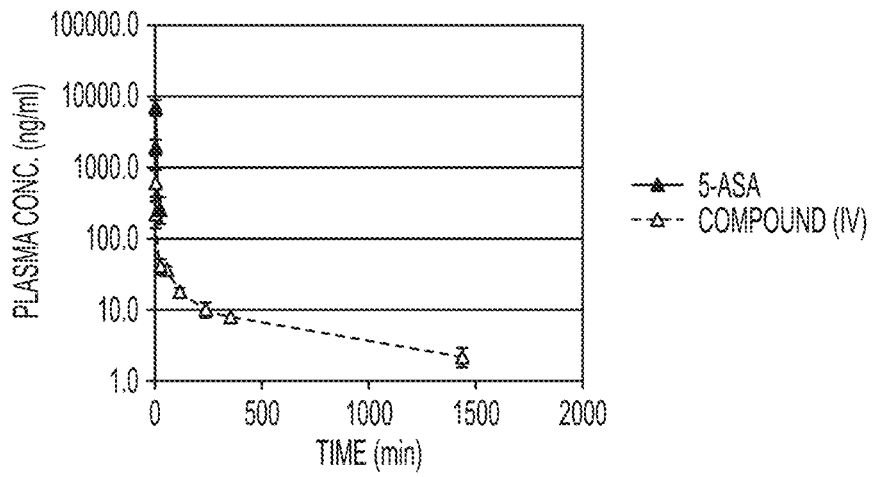
FIG. 3. Comparison of the kinetic profiles of the compound (IV) and the 5-ASA metabolite thereof after i.v. administration of the 5-ASA butyrate.
Figure 4:
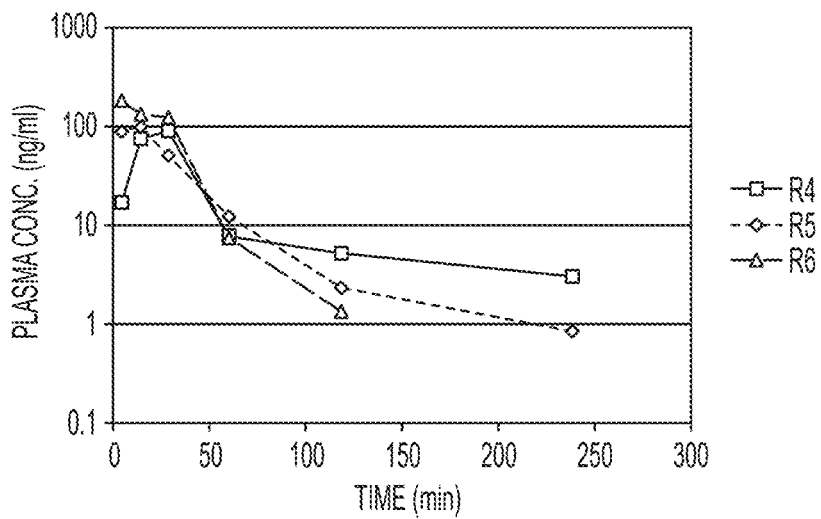
FIG. 4. Kinetic profiles of the 5-ASA butyrate after oral administration 50 mg/kg.
Figure 5:
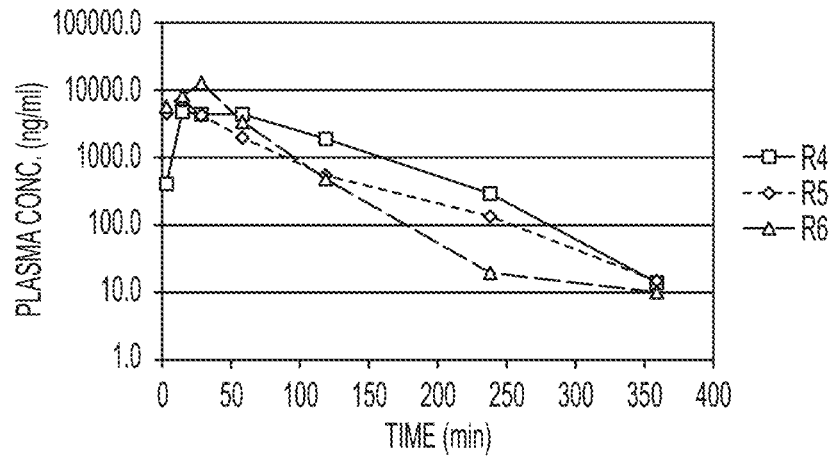
FIG. 5. Kinetic profiles of the 5-ASA metabolite after oral administration of the 5-ASA butyrate, 50 mg/kg.
Figure 6:
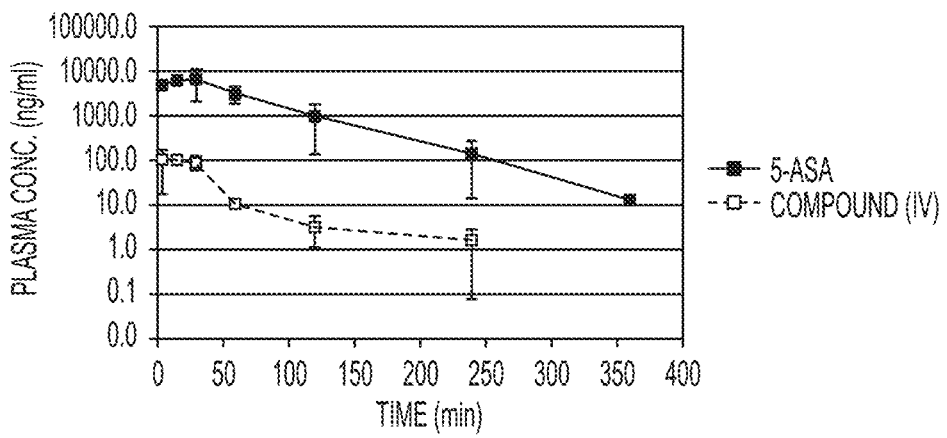
FIG. 6. Comparison of the kinetic profiles of the 5-ASA butyrate and of the 5-ASA metabolite thereof after oral administration of the 5-ASA butyrate.
Figure 7A:
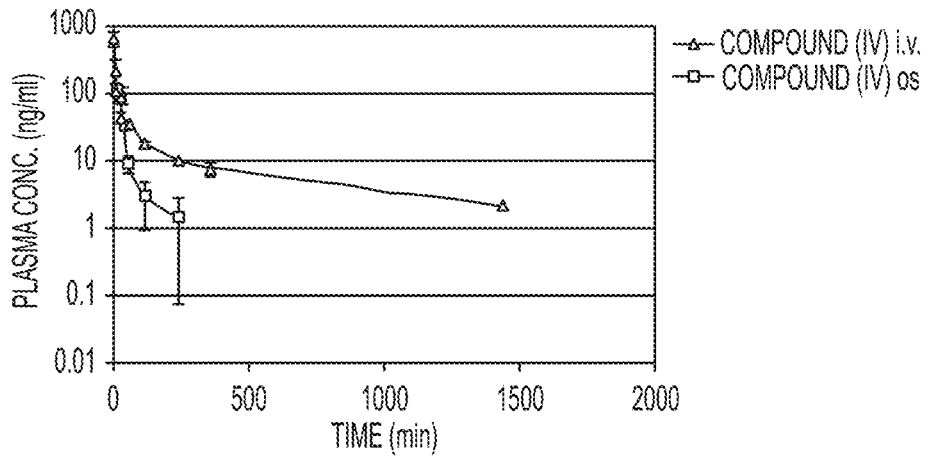
FIG. 7. Comparison of the kinetic profiles of the 5-ASA butyrate and of the 5-ASA metabolite thereof after A) i.v. administration and B) oral administration 50 mg/Kg of the 5-ASA butyrate.
Figure 7B:
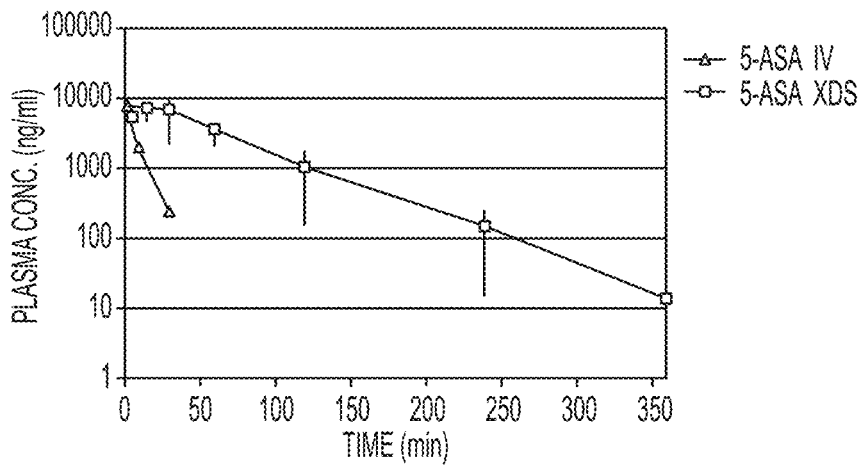

An object of the present invention is represented by the compounds corresponding to the following general formula (I):

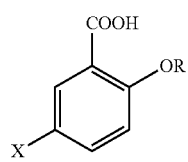

wherein:
R=$C_4$-$C_8$ alkanoyl; and
X=NH—$R_1$
where $R_1$=H, or protecting group for amines, preferably the tert-butyloxycarbonyl group (Boc);
and/or the pharmaceutically acceptable salts thereof.

The expression "protecting group for amines" refers to the text "Greene and Wuts, Protective Groups in Organic Synthesis, Third edition, pages. 503-648", incorporated herein for reference.

Preferred compounds according to the present invention are represented by the following formula (Ia):

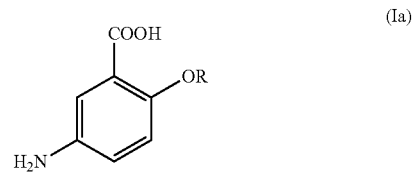

wherein:
R=$C_4$-$C_8$ alkanoyl;
and/or the pharmaceutically acceptable salts thereof.

In a preferred embodiment, an object of the present invention is to provide 5-amino-2-(butyryloxy)benzoic acid and/or the pharmaceutically acceptable salts thereof, preferably hydrochloride salt (compound (IV)).

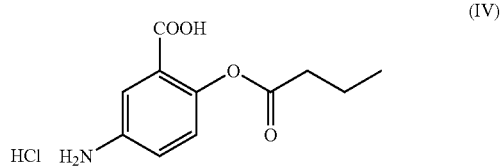 [SMILES: Cl ; CCCC(=O)Oc1ccc(N)cc1C(=O)O]

The compounds of formula (Ia), in particular 5-amino-2-(butyryloxy)benzoic acid and/or the pharmaceutically acceptable salts thereof, preferably hydrochloride salt, as a medicament form a further object of the present invention.

In particular, said 5-amino-2-(butyryloxy)benzoic acid and/or the pharmaceutically acceptable salts thereof intervene as prodrugs capable of releasing the two active ingredients, mesalazine and butyric acid, in the selective sites of the intestinal idiopathic flogosis, distal ileum and colon.

The compounds of formula (Ia), in particular 5-amino-2-(butyryloxy)benzoic acid and/or pharmacologically useable salts thereof, for use in the treatment of acute and chronic intestinal inflammatory diseases, among which IBD (Inflammatory Bowel Disease), ulcerative colitis, Crohn's disease, diverticular disease, IBS (Irritable Bowel Syndrome) form a further object of the present invention. Preferably, the compounds of formula (Ia) are specifically applied in the treatment of IBD.

According to the present invention the aforementioned compounds of formula (Ia) and, in particular 5-amino-2-(butyryloxy)benzoic acid and/or the pharmaceutically useable salts thereof, can be administered to human beings, intended both as an adult subject and as "paediatric population", where the term "paediatric population" is used to indicate the part of population between birth and eighteen years of age.

A pharmaceutical composition containing the compounds of formula (Ia), in particular 5-amino-2-(butyryloxy)benzoic acid and/or the pharmaceutically acceptable salts thereof, and at least one physiologically acceptable excipient form a further object of the present invention.

Actually, the compounds according to the present invention can be administered to patients affected by acute and chronic intestinal inflammatory diseases, in form of pharmaceutical preparations taking into account the local and nonsystemic activity of these active ingredients. The expression "local activity" is used to indicate that the active ingredient should come to contact with the mucosa of the colon.

Said pharmaceutical composition may contain the aforementioned compounds in solid form, preferably selected from among tablet, capsule, granule, microgranule, in semi-solid form, preferably selected from among suppository, gel or ointment for rectal administration or topical anal application or in liquid form, preferably selected from among suspension or aqueous solution for oral administration or for rectal administration preferably through enema, or rectal foam.

Oral administration may use modified-release preparations which go through the stomach or small intestine unaltered and then release the active ingredient in the colon.

Administration of the pharmaceutical composition according to the present invention is particularly advantageous in that it allows administering the anti-inflammatory 5-ASA and the intestinal trophic factor, butyric acid, in a single administration, thus improving the patient compliance with respect to a combined administration of the two active ingredients separately.

The in vitro and in vivo tests, indicated below in the experimental part, reveal some considerable characteristics of 5-amino-2-(butyryloxy)benzoic acid in form of hydrochloride salt, the compound (IV).

It is stable in storage both in the normal (25° C., 60% RH) and accelerated conditions (40° C., 75% RH) as well as in the gastric and in the simulated intestinal fluids; it has a high hydrolysis percentage in both human and murine plasma; it has low permeability through the basolateral membrane of the Caco2 cell line, hence guaranteeing maintaining the topic action of 5-ASA to be released; furthermore, it is quickly metabolised in the rat intestine.

In vivo pharmacokinetic studies in rats wherein the compound (IV) is administered p.o. and i.v. revealed good pharmacokinetic parameters thereof.

The same in vitro and in vivo studies carried out on another conjugated derivative of mesalazine with butyric acid, in particular the derivative of formula (IIIb):

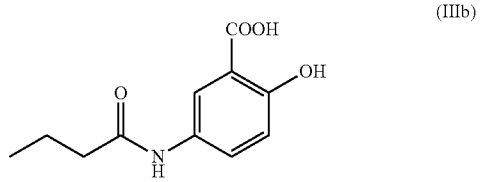 [SMILES: CCCC(=O)Nc1ccc(O)c(C(=O)O)c1]

(IIIb)

on the contrary did not reveal positive results.

This shows that not all conjugates of mesalazine with butyric acid are suitable for the treatment of intestinal disease.

A further object of the present invention is the process of synthesis of the compounds of formula (Ia) characterised by the following steps:

a') protection of 5-ASA with an amine protecting group to obtain the compounds of formula (II');

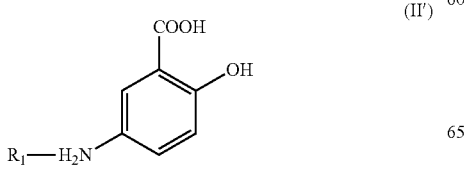

(II')

b') acylation of the hydroxyl group of the compounds of formula (II') to obtain the compounds of formula (III');

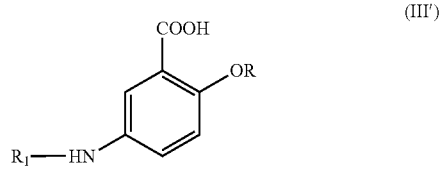

(III')

c') deprotection of the amino group.

wherein:

R=$C_4$-$C_8$ alkanoyl;

and $R_1$ is an amine protecting group, preferably the tert-butyloxycarbonyl group (Boc).

In particular, Scheme A reported below, shows the preferred synthesis for obtaining 5-amino-2-(butyryloxy)benzoic acid, in form of hydrochloride (compound IV), starting from 5-ASA:

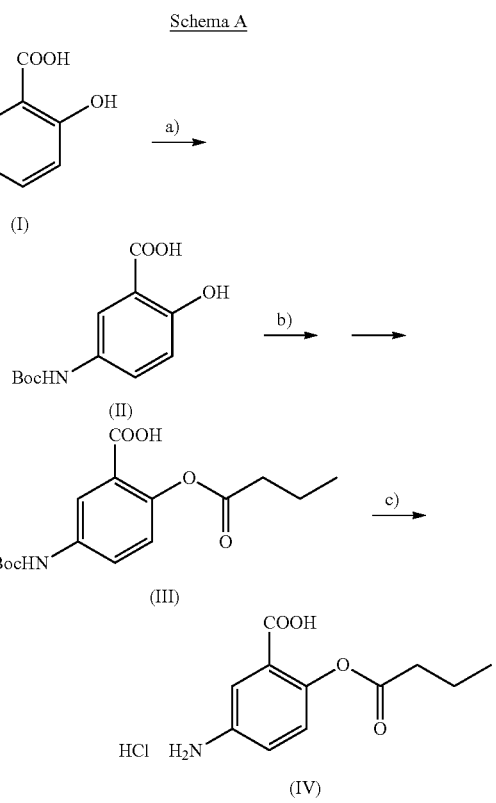

Schema A

Such process is characterised by the following steps:

a) protection of 5-ASA as a Boc-derivative to obtain the compound (II);

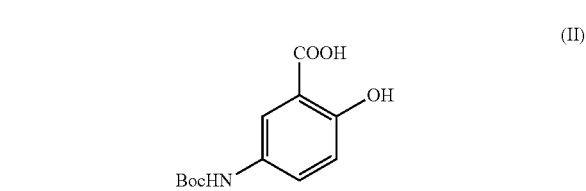 [SMILES: CC(C)(C)OC(=O)Nc1ccc(O)c(C(=O)O)c1]

(II)

b) butyrylation of the hydroxyl group of the compound (II) to obtain the compound (III);

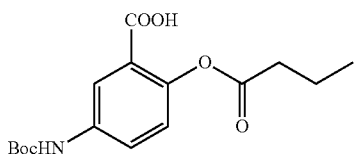 (III)

c) deprotection of the amino group of the compound (III) to obtain 5-amino-2-(butyryloxy)benzoic acid as hydrochloride, compound (IV).

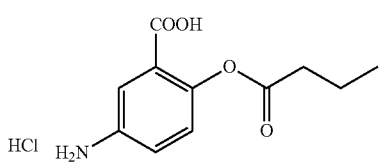 (IV)

The step a) is conducted in an aprotic polar solvent and/or in a mixture of said solvent with $H_2O$, preferably in a molar ratio comprised between 1:1 and 3:1, more preferably 2:1. Said mixture is preferably constituted by dioxane and water, preferably in a 2:1 molar ratio. Such step is conducted in presence of a base, preferably organic, more preferably triethylamine in a molar ratio comprised between 1:1 and 3:1, preferably 1.5:1 with respect to the 5-ASA. Di-tert-butyl dicarbonate ($Boc_2O$) is used in a molar ratio comprised between 1:1 and 2:1, preferably 1.5:1 with respect to the 5-ASA.

The step b) is conducted in presence of a butyryl halide, preferably butyryl chloride and/or butyric anhydride in a molar ratio comprised between 1:1 and 3:1, preferably 2:1 with respect to the compound (II).

The step b) is conducted in an aprotic apolar solvent, preferably selected from among an aliphatic or aromatic hydrocarbon, halogenated aliphatic hydrocarbon, more preferably dichloromethane, in presence of a base, preferably organic, more preferably diisopropylethylamine, preferably in a 3:1 molar ratio with respect to the compound (II).

The step of deprotection c) is conducted in an acidic environment preferably generated by HCl in an aprotic solvent, more preferably by HCl in dioxane or HCl in ethyl ether.

Alternatively, the compounds of formula (Ia) can be synthesised according to the following steps:

d') acylation of the hydroxyl group of the nitro derivative (V') available in the market

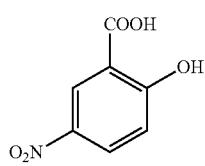 (V')

to obtain the compounds of formula (VI');

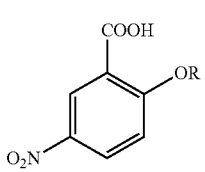 (VI')

e') hydrogenation of the nitro group of the compounds of formula (VI')
wherein:
R=$C_4$-$C_8$ alkanoyl.

In particular, Scheme B reported below shows the synthesis for obtaining the 5-amino-2-(butyryloxy)benzoic acid starting from (V'):

Schema B

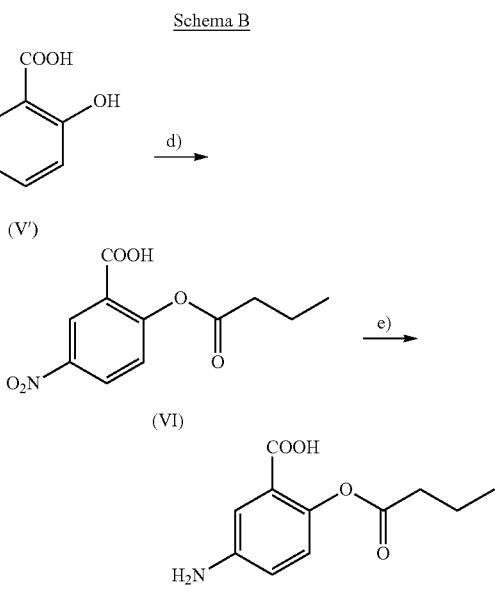

Such process is characterised by the following steps:
d) butyrylation of the nitro derivative (V')

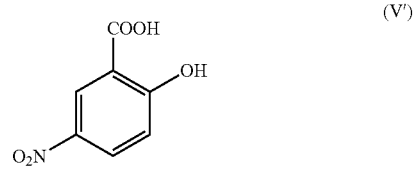 [SMILES: O=C(O)c1cc([N+](=O)[O-])ccc1O] (V')

to obtain the compound (VI);

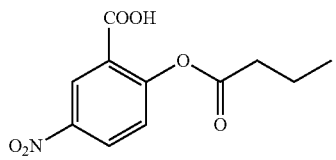 (VI)

e) hydrogenation of the compound (VI) to obtain 5-amino-2-(butyryloxy)benzoic acid.

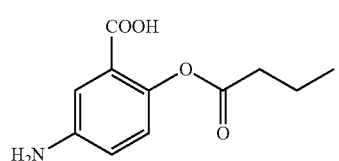

The step d) is conducted in presence of butyric anhydride and/or a butyryl halide, preferably butyric anhydride, preferably in presence of an acid catalysis, preferably sulfuric acid. Said butyric anhydride is used in a molar ratio with respect to the compound (V') comprised between 1:1 and 5:1, preferably 3:1. Said step d) is conducted at a temperature comprised between 40° C. and 70° C., preferably about 55° C.

The step d) is conducted in a polar solvent, preferably in a $C_1$-$C_4$ alcohol, dioxane, tetrahydrofuran and/or mixtures thereof. Said $C_1$-$C_4$ alcohol is preferably ethanol.

The compound corresponding to the formula (Ib) indicated below

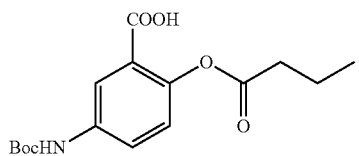

(Ib)

and the use thereof as an intermediate in the synthesis processes indicated above is also an object of the present invention.

The examples below are intended to be illustrative and not limiting of the present invention.

EXAMPLES

Example 1

Synthesis of the 5-(tert-butoxycarbonylamino)-2 hydroxybenzoic acid (II)

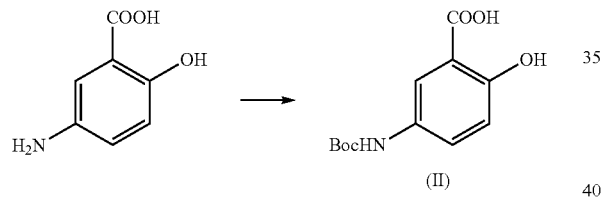

(II)

Triethylamine (1.5 eq) (complete dissolution) followed by di-tert-butyl dicarbonate (1.5 eq) are added to a suspension of about 0.27 M of 5-ASA in a 2:1 dioxane/water mixture, cooled to 0° C. It is stirred for 30 min at 0° C. and at ambient temperature for 16 hours. Dioxane is evaporated, the aqueous resulting solution is cooled in an ice bath and acidified with HCl 3N. The product (II) precipitates as white solid. It is filtered, it is washed with water, it is dried under vacuum at 50° C. Quantitative yield.

Example 2

Synthesis of 5-(tert-butoxycarbonylamino)-2-(butyryloxy)benzoic acid (III)

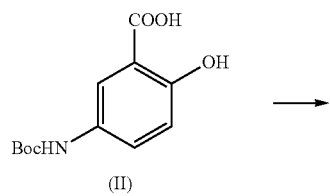

(II)

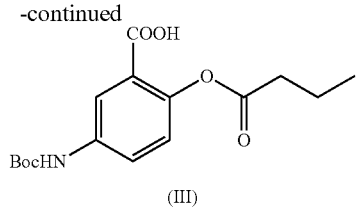

(III)

Diisopropylethylamine (3 eq) (complete dissolution) followed by butyryl chloride (2 eq) is added to a suspension of about 0.4 M of the compound (II) in dichloromethane, cooled to 0° C. and in inert atmosphere. It is stirred at ambient temperature for 16 hours. HCl 1N (cooled in an ice bath) up to acid pH is added. The organic phase is washed with water, anhydrified and evaporated. At this stage a mixture of the desired product (III) and deacylated product (probably the corresponding anhydride) is obtained as a whitish solid. The mixture is dissolved in ethyl ether (concentration of about 0.1 M), a 2N solution of HCl in ethyl ether (0.2 eq) is added and it is stirred at ambient temperature for 25 days, during which 2N hydrochloride ether is added other 2 times (0.4 eq HCl totally) up to obtaining complete conversion in the product (III). The solvent is evaporated, the resulting solid is triturated with hexane (2 times), it is filtered and it is dried, obtaining the product (III) as white solid. 88% yield, LC-MS 99% purity.

Example 3

Synthesis of the hydrochloride of the 5-amino-2-(butyryloxy)benzoic acid (IV)

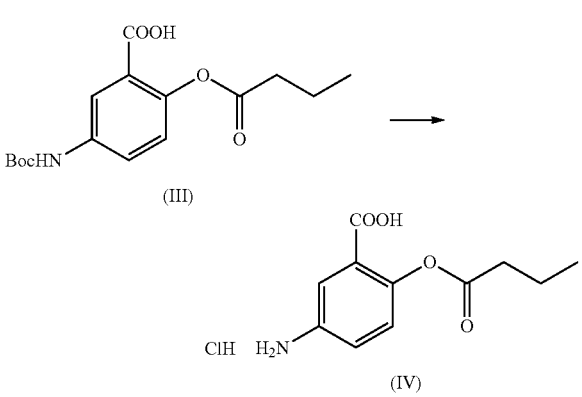

A 4N solution of HCl in dioxane (5 eq HCl) is added to a solution of about 0.07 M of the compound (III) in ethyl ether; it is stirred at ambient temperature for 20 days, during which hydrochloride dioxane is added periodically and hence 2N HCl in ethyl ether (10 eq HCl totally) and there is a gradual precipitation of the product. It is filtered by washing abundantly with ethyl ether, it is dried at ambient temperature, obtaining (IV) as a light beige solid. 65% yield, LC-MS 98% purity.

If necessary, the product can be triturated in an ethyl ether/dioxane mixture (3:1 respectively) to increase the titre thereof.

$^1$H NMR (300 MHz, DMSO-$d_6$) δ ppm 7.64 (d, 1H), 7.33 (dd, 1H), 7.14 (d, 1H), 2.52-2.55 (m, 2H), 1.65 (sxt, 2H), 0.97 (t, 3H).

Experimental Part

Example 4

Evaluation of the Stability of the Compound (IV) at 25° C. and at 40° C.

The object of such study is the evaluation of the stability of the compound (IV) kept at a temperature equivalent to 25° C. (60% RH) and at 40° C. (75% RH). In particular, such study aims at evaluating the titre of the compound (IV) in the stability test at 25° C. (60% RH) at 3, 6, 9, 12, 18, 24, 36, 48, 60 months and in the stability test accelerated at 40° C. (75% RH) at 3, 6, 9, 12 months.

The compound (IV) is divided into 10 Eppendorfs numbered from 1 to 10, containing about 50 mg of product and stored in a cellar at 25° C. 60% RH.

Other 4 Eppendorfs numbered from 11 to 14, containing about 50 mg of product are introduced into an oven at a temperature equivalent to 40° C. 75% RH.

The titre at time t=0 is equivalent to 99.3%.

Currently there data are available at 3 months, indicated in the Tables 1 and 2.

TABLE 1

Compound (IV) at 25° C. 60% RH

| | Samp P (mg) | Area 1 | Area 2 | Mean area | Titre % |
|---|---|---|---|---|---|
| Sample 1 | 10.2 | 79.42 | 79.45 | 79.43 | 98.2 |
| Sample 2 | 10.3 | 79.88 | 80.42 | 80.15 | 98.1 |
| | | | | Mean | 98.1 |

TABLE 2

Compound (IV) at 40° C. 75% RH

| | Samp P (mg) | Area 1 | Area 2 | Mean area | Titre % |
|---|---|---|---|---|---|
| Sample 1 | 10.5 | 83.22 | 83.06 | 83.14 | 99.8 |
| Sample 2 | 10.5 | 85.52 | 85.40 | 85.46 | 102.6 |
| | | | | Mean | 101.2 |

From the experimental results obtained up to date, the compound (IV) does not seem to be subjected to considerable modifications in the two storage conditions.

Example 5

Evaluation of the Stability of the Compound (IV) in Simulated Gastric and Simulated Intestinal Fluids Such study is conducted with the aim of evaluating the stability of the compound (IV) at 1.1 pH (SIF) and 7.4 pH (SGF) in absence of enzymes of the intestinal bacterial flora.

The stability of the compound (IV) is compared to that of known reference standards.

Table 3 shows experimental results indicating that the molecule is stable in both media (SIF and SGF) both after 30 and 90 minutes from incubation.

TABLE 3

Residual percentage of the compound (IV) after 30 and 60 minutes of incubation in SIF and SGF

| | SGF % Residue | | SIF % Residue | |
|---|---|---|---|---|
| Compounds | 30 min | 60 min | 30 min | 60 min |
| Compound (IV) | 97.3 ± 1.1 | 99.9 ± 0.9 | 97.4 ± 4.1 | 103.2 ± 3.5 |
| Rifampicin | 84.9 ± 1.5 | 65.8 ± 1.5 | 98.9 ± 1.1 | 94.2 ± 1.1 |
| Erythromycin | 0.2 ± 0.1 | 0.1 ± 0.1 | 98.1 ± 1.4 | 100.9 ± 0.4 |
| Chlorambucil | 92.8 ± 2.1 | 89.8 ± 1.5 | 42.1 ± 0.5 | 13.9 ± 0.3 |

SGF = Simulated Gastric Fluid
SIF = Simulated Intestinal Fluid
The values are expressed as mean ± SD (n = 2)

Example 6

Evaluation of the Stability of the Compound (IV) in Human and Rat Plasma

Such study is conducted with the aim of evaluating possible hydrolysis of the compound (IV) by the plasma esterases.

The percentage of hydrolysis of the compound (IV) is compared to that of known reference standards.

The obtained experimental results, indicated in Table 4, indicate that in the human plasma the compound (IV) is 67.3% hydrolysed while in murine plasma it is 91.5% hydrolysed, after 1 hour of incubation.

TABLE 4

Results of the stability in human and murine plasma of the compound (IV)

| | Rat plasma | Human plasma |
|---|---|---|
| Compounds | % Residue at 60 min | |
| Compound (IV) | 8.5 ± 2.0 | 32.7 ± 2.6 |
| M7319 | 0.20 ± 0.03 | 10.8 ± 0.1 |
| Lidocaine | 93.4 ± 4.9 | 105.0 ± 12.1 |

The results are expressed as mean ± SD (n = 2)
Values exceeding 100% are possibly due to the matrix effect

Example 7

Evaluation of the Permeability of the Compound (IV) on the Caco2 Cellular Line Such study is conducted with the aim of evaluating the capacity of the molecule to permeate the intestinal epithelium and be absorbed thereby evaluating the Papp (apparent permeability coefficient).

The Papp of the compound (IV) is compared to that of the known reference standards.

Table 5 shows the obtained experimental results. They indicate that the molecule has poor permeability and that there are no apparent reflux phenomena (BA/AB<1 ratio). Hence, the product does not seem to be a substrate of P-gp (glycoprotein P), hence guaranteeing maintaining the topic action of the active ingredient, 5-ASA, to be released.

TABLE 5

Permeability data

| Compounds | Papp A→B (nm/sec) Mean ± SD | A→B Mean mass balance % | Papp B→A (nm/sec) Mean ± SD | B→A Mean mass balance % | BA/AB ratio |
|---|---|---|---|---|---|
| Compound (IV) | 5.9 ± 1.2 | 69 | 2.4 ± 0.3 | 99 | 0.41 |
| Cimetidine | 5.8 ± 0.4 | 63 | 24.5 ± 3.4 | 111 | 4.2 |
| Vinblastine | 4.1 ± 2.1 | 89 | — | — | — |
| Caffeine | 341.4 ± 14.8 | 83 | — | — | — |

The results are expressed as mean ± SD (n = 2)
Apical (pH 6.5) → Basolateral (pH 7.4)
Classification of absorption: Papp >50: High; Papp 10-50: Medium; Papp <10: Low Example 8

Evaluation of the Stability of the Compound (IV) in Murine Intestinal Homogenate Such study is conducted with the aim of evaluating the stability of the compound (IV) in intestinal homogenate.

The stability of the compound (IV) is compared to that of known reference standards.

The obtained experimental results, indicated in Table 6 below, indicated that the compound (IV) is very unstable in the rat intestine, i.e. it is metabolized very quickly. In particular, the compound (IV) tested at two concentrations (25 and 50 μM) shows a hydrolysis concentration exceeding 90-95%.

TABLE 6

Residue percentage of the compound (IV) in rat intestinal homogenate after 30 min, 1, 2 and 4 hours of incubation.

| Compounds | Rat intestine | | | |
|---|---|---|---|---|
| | 30 min | 1 hr | 2 hrs | 4 hrs |
| Compound (IV) 25 μM | 9.8 ± 1.1 | 12.2 ± 1.6 | 10.1 ± 4.4 | 24.5 ± 1.3(*) |
| Compound (IV) 50 μM | 5.6 ± 0.6 | 4.4 ± 1.1 | 7.3 ± 1.0 | 5.5 ± 1.1 |
| Chlorambucil | 49.5 ± 7.8 | 16.9 ± 2.2 | 1.5 ± 0.1 | 0.20 ± 0.08 |
| Erythromycin | 83.5 ± 3.6 | 84.7 ± 3.6 | 95.0 ± 11.0 | 97.5 ± 2.8 |

The results are expressed as mean ± SD (n = 2)
(*)The increase detected at this last point could be due to injection problems.

Example 9

Evaluation of the Hydrolysis of the Compound (IV) in Rat Intestine Preserved in Different Conditions Such study is conducted with the aim of surveying the stability of the compound (IV) in rat intestine homogenate preserved in different conditions: frozen at 4° C. and at −80° C.

The stability of the compound (IV) is compared to that of known reference standards.

The obtained experimental results, indicated in Table 7 below, indicated that the compound (IV) in the fresh rat intestine homogenate is metabolised quickly. The same enzymatic activity is observed in the homogenate preserved at 4° C. and at −80° C. after three weeks.

TABLE 7

Residual percentage of the compound (IV) in rat intestine after 15, 30 and 60 min of incubation

| Compound/ conditions | Stability in rat intestine (residue %) | | |
|---|---|---|---|
| | 15 min | 30 min | 60 min |
| Compound (IV) fresh homogenate | 0.030 ± 0.015 | 0.031 ± 0.004 | 0.047 ± 0.021 |
| Compound (IV) homogenate 4° C. | 0.046 ± 0.004 | 0.046 ± 0.022 | 0.064 ± 0.008 |
| Compound (IV) homogenate −80° C. | 0.024 ± 0.007 | 0.034 ± 0.001 | 0.470 ± 0.012 |
| Compound (IV) intestine −80° C. | 0.145 ± 0.029 | 0.091 ± 0.038 | 0.098 ± 0.002 |
| Chlorambucil fresh homogenate | 75.2 ± 3.8 | 58.7 ± 2.3 | 28.0 ± 1.5 |
| Chlorambucil homogenate 4° C. | 76.5 ± 5.0 | 53.0 ± 13.9 | 25.9 ± 5.3 |
| Chlorambucil intestine −80° C. | 73.0 ± 1.2 | 25.0 ± 6.1 | 6.9 ± 1.4 |

The results are expressed as mean ± SD (n = 2)

Example 10

Evaluation of the in Vivo Pharmacokinetic of the Compound (IV)

The objectives of such study are the evaluation of the most relevant pharmacokinetic parameters (Cmax, Tmax, AUC, clearance, half-life and bioavailability after i.v. and p.o. administration) of the compound (IV) in the rat and the quantification of the product 5-ASA (metabolite of the compound (IV)) after administration of the compound (IV).

Tables 8 and 9 indicate the obtained experimental data.

They indicate that the compound (IV) is metabolised quickly after i.v. and p.o. treatment. An abundant amount of the metabolite thereof, 5-ASA, is observed in the plasma. After i.v. administration the amount of 5-ASA in the plasma is ten times greater than that of the compound (IV) with a range of concentration in the plasma comprised between 659 and 2.1 ng/ml.

After p.o. administration, the compound (IV) reveals a Cmax between 5 and 30 min. equivalent to 95 ng/ml and reduces up to 1 ng/ml after 4 hours. The levels of metabolite 5-ASA are 50 times greater than those of the compound (IV).

TABLE 8

Pharmacokinetic parameters of the compound (IV) after i.v. administration (5 mg/kg) and oral gavage (50 mg/kg) in the rat

| IV | Rat 1 | Rat 2 | Rat 3 | Mean | SD | CV % |
|---|---|---|---|---|---|---|
| AUCinf (min*ng/ml) | 20455 | 18700 | 22424 | 20526 | 1863.1 | 9.1 |
| AUClast (min*ng/ml) | 17757 | 17271 | 21300 | 18776 | 2199.4 | 11.7 |
| Tmax (min) | 2 | 2 | 2 | 2 | — | — |
| Tlast (min) | 1440 | 1440 | 1440 | 1440 | — | — |
| Cmax (ng/ml) | 598 | 529 | 851.2 | 659 | 169.7 | 25.7 |
| Clast (ng/ml) | 2.9 | 1.8 | 1.7 | 2.1 | 0.7 | 31.2 |
| T½ (min) | 638.5 | 547.1 | 451.8 | 545.8 | 93.3 | 17.1 |
| MRT (min) | 273 | 209 | 175 | 219 | 50 | 23 |
| Cl (ml/min/kg) | 210.2 | 229.9 | 191.8 | 210.6 | 19.1 | 9.1 |
| Vdss (L/kg) | 115.3 | 83.5 | 51.9 | 83.5 | 31.6 | 37.8 |

TABLE 8-continued

Pharmacokinetic parameters of the compound
(IV) after i.v. administration (5 mg/kg)
and oral gavage (50 mg/kg) in the rat

| XOS | Rat 4 | Rat 5 | Rat 6 | Mean | SD | CV % |
|---|---|---|---|---|---|---|
| AUCinf (min*ng/ml) | 4593 | 3985 | 5954 | 4844 | 1008 | 24.1 |
| AUClast (min*ng/ml) | 4042 | 3943 | 5925 | 4637 | 1117 | 24.1 |
| Cmax | 89 | 104 | 174 | 122 | 45.4 | 37.1 |
| Tmax (min) | 30 | 15 | 5 | 16.7 | 12.6 | 75.5 |
| Clast (ng/ml) | 2.9 | 0.8 | 1.3 | 2.8 | 1 | 37.1 |
| Tlast (min) | 240 | 240 | 120 | 200 | 69 | 34 |
| MRTlast (min) | 48 | 32 | 23 | 35 | 11.6 | 33.3 |
| Mean Fpo 0_inf (%) | | | | 2.4 | | |

AUCinf = area below the lower curve;
AUClast = area below the last curve;
Cmax = maximum concentration;
Tmax = time corresponding to the Cmax;
Clast = last concentration;
Tlast = time corresponding to the Clast;
T½ = time of half-life;
MRT = mean residence time;
Cl = Clearance;
Vdss = volume of distribution at stationary state;
Mean Fpo = mean p.o. bioavailability.

TABLE 9

Pharmacokinetic parameters of 5-ASA after i.v. and oral gavage
administration of the compound (IV) respectively at 5 and 50 mg/Kg.

| | Mean |
|---|---|
| IV | |
| AUCinf (min * ng/ml) | 84541 |
| AUClast (min * ng/ml) | 82431 |
| Tmax (min) | 2 |
| Tlast (min) | 30 |
| Cmax (ng/ml) | 7878 |
| Clast (ng/ml) | 252 |
| X OS | |
| AUCinf (min * ng/ml) | 532323 |
| AUClast (min * ng/ml) | 524216 |
| Cmax (ng/ml) | 6962 |
| Tmax (min) | 15 |
| Tlast (min) | 240 |

Parameters calculated on the mean concentrations of 5-ASA

Example 11

Experimental Protocol for the Efficacy Evaluation of Compound (IV) in the Treatment of Intestinal Inflammatory Disease Experimental colitis models, such as the dextran sodium sulphate (DSS) model, are routinely available in our laboratory (1, 2). The DSS-induced colitis model has been generally accepted and used to screen pharmaceutical drugs at preclinical level for the treatment of inflammatory bowel disease (3) and it exhibits some of the clinical and histological inflammatory features which are found in humans with ulcerative colitis. DSS-induced inflammation of the colon originates in the distal colon, progressing to involve the whole colon and in severe cases the caecum. In addition, the inflammation is confined to the mucosa and is generally not transmural. Furthermore, DSS-induced inflammation is not dependent on the presence of any specific intestinal bacterial flora. DSS-induced inflammation has been shown to be mitigated by treatment with experimental therapeutic principles, for example, the immuno-suppressant FK506 (4) and it also responds favorably to treatment with cyclosporine, an immunosuppressant drug which is used to treat inflammatory bowel disease in humans (5). Sulphasalazine (SASP) and olsalazine (OLZ) are 5-aminosalicylic acid (5-ASA) based drugs have also been found able to ameliorate the DSS-induced intestinal inflammation (3). The dose-response patterns suggested that the active therapeutic moiety for the two drugs appears to be mainly the liberated 5-ASA molecule.

On the basis of the above background we have evaluated the therapeutic effect of selected compounds, namely 5-ASA, 5-ASA-butyrate (compound (IV)), butyric acid, and 5-ASA and butyric acid (administered separately) through said colitis model. Colon inflammation has been induced in C57BL/6 mice by the administration of DSS in the drinking water at concentrations of 3%, for 5 days.

Several experimental protocols (8 animals per group) have been used for evaluating the therapeutic effect of the aforementioned selected compounds, when compared to placebo either in the active or in the remission phase of the inflammatory disease:

DSS 3%+5-ASA orally every day
DSS 3%+5-ASA-butyrate (compound (IV)) orally every day
DSS 3%+butyric acid orally every day
DSS 3%+placebo orally every day
DSS 3%+5-ASA+butyric acid (administered separately) orally every day Different parameters have been measured to test the efficacy of the selected compounds which are:

Clinical evaluation: daily recording weight and clinical activity (anal bleeding, presence of diarrhoea). This parameter has been quantified as percentage of body weight and DAI (Disease Activity Index) relating to anal bleeding and presence of diarrhoea. The lower the DAI is, the lower the anal bleeding is, thus better the therapeutic effect is.

Endoscopic evaluation: mice underwent endoscopy at the end of the treatment. This step is very important as most of the drugs used in human inflammatory bowel disease aim to achieve mucosal healing.

Histological colitis assessment: mice have been sacrificed at the end of the treatment, colons have been removed and histopathological analysis has been performed to assess the extent of tissue damage and recruitment of immune cells.

Endoscopic and histological scores as well as the colon length are reported for each administered dose so as to assess the efficacy of the tested compounds in the colitis model.

Figure 8A:
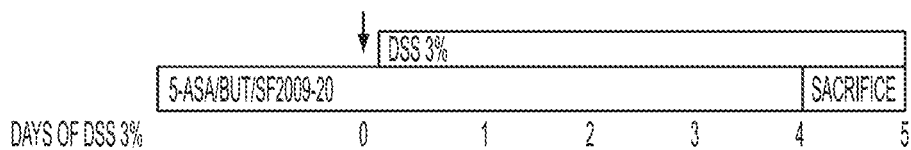
FIG. 8: Experimental results after oral administration of 50 mg/kg of 5-ASA; butyric acid; 5-ASA butyrate; placebo; 5-ASA and butyric acid.
Figure 8B:
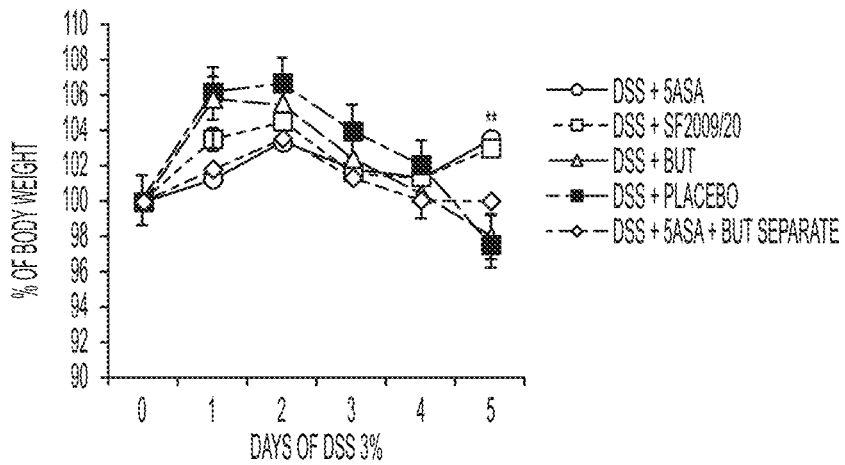
Figure 8C:
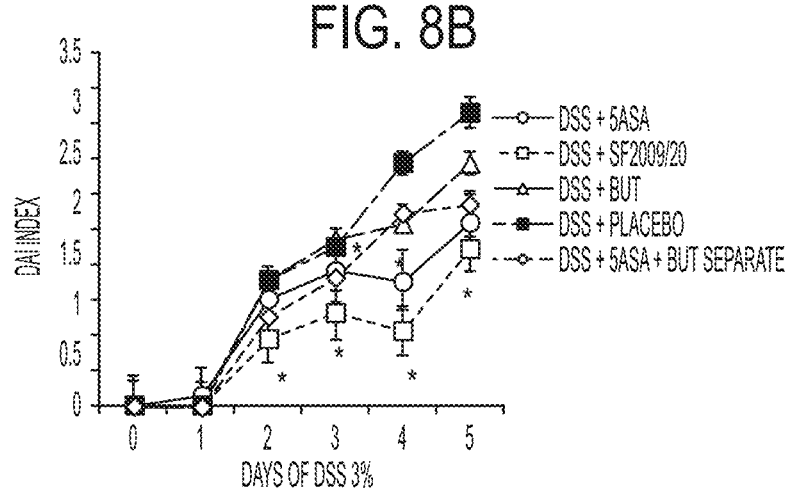
Figure 9A:
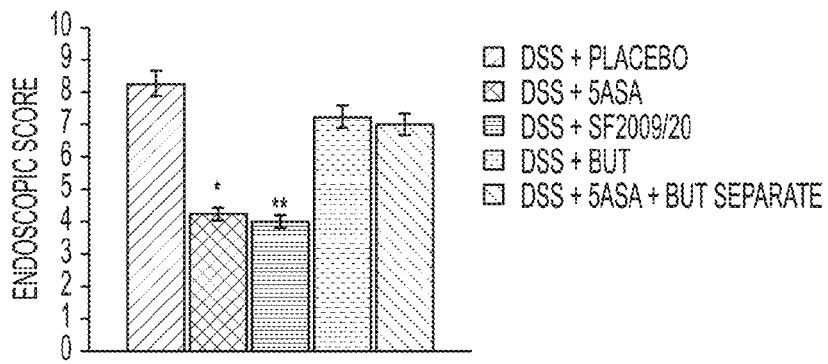
FIG. 9: Endoscopic and histological scores for experiments after oral administration of 50 mg/kg of 5-ASA; butyric acid; 5-ASA butyrate; placebo; 5-ASA and butyric acid.
Figure 9B:
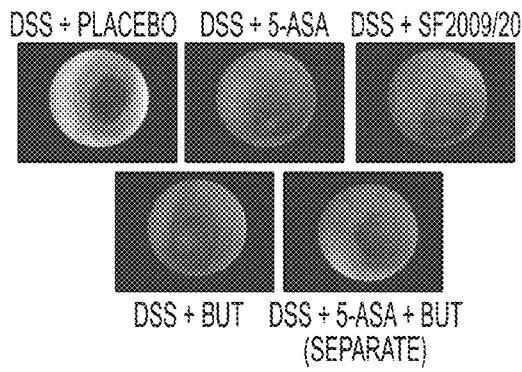
Figure 9C:
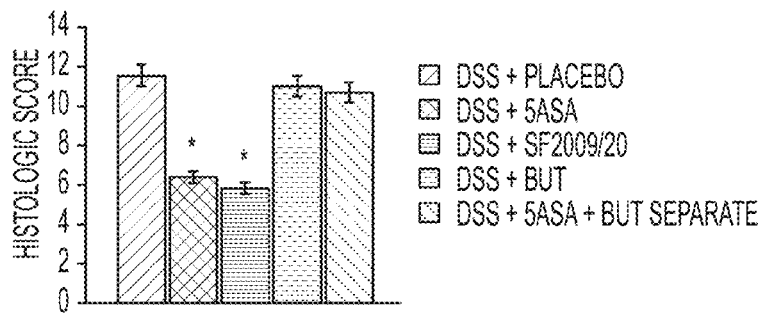
Figure 9D:
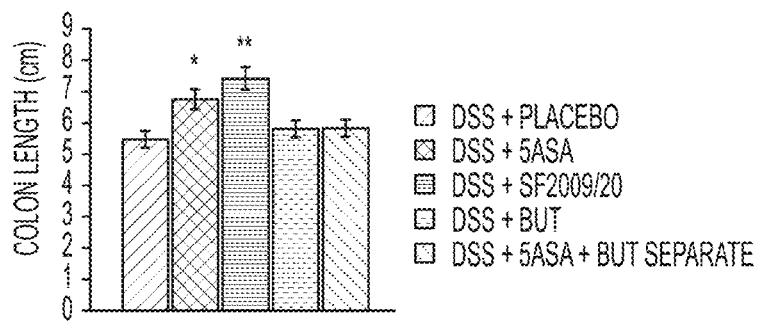
Figure 10A:
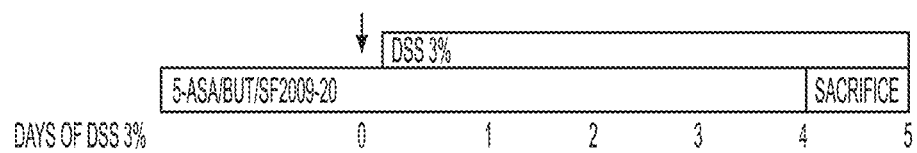
FIG. 10: Experimental results after oral administration of 100 mg/kg of 5-ASA; butyric acid; 5-ASA butyrate; placebo; 5-ASA and butyric acid.
Figure 10B:
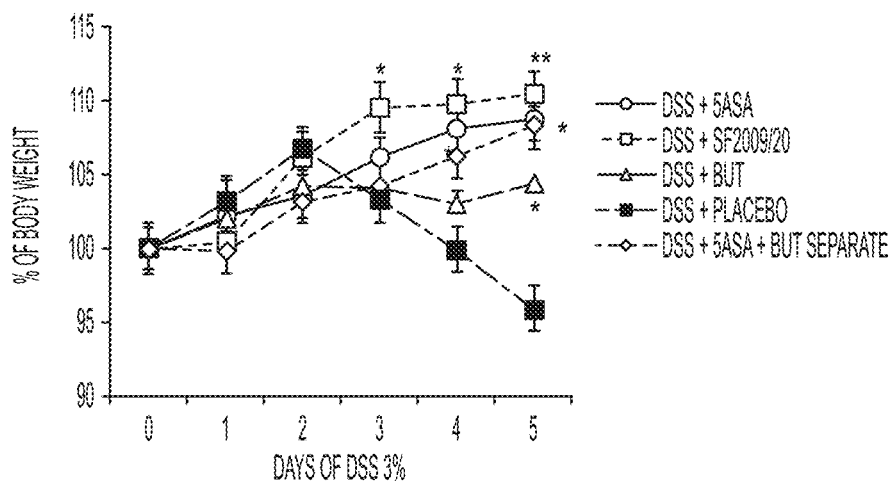
Figure 10C:
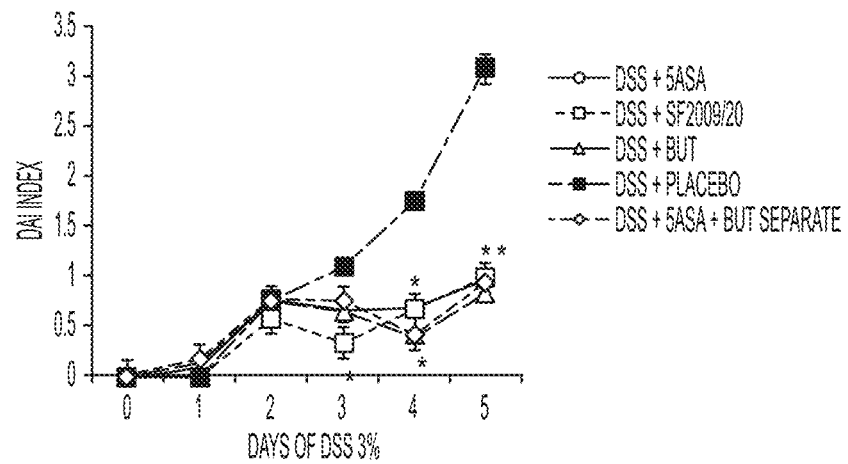
Figure 11A:
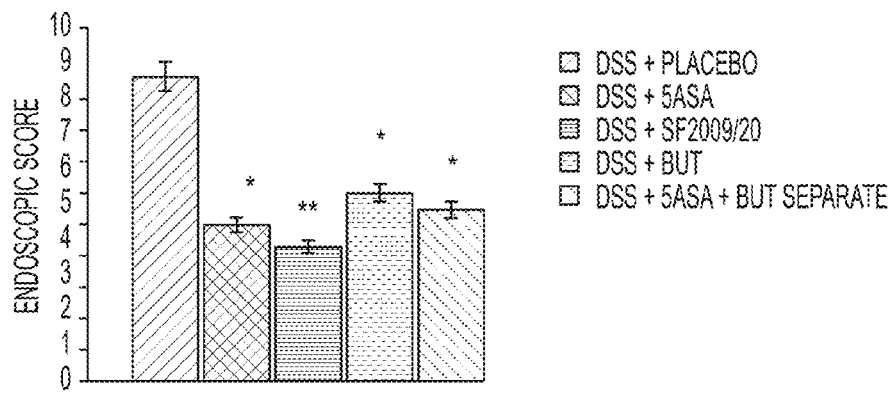
FIG. 11: Endoscopic and histological scores for experiments after oral administration of 100 mg/kg of 5-ASA; butyric acid; 5-ASA butyrate; placebo; 5-ASA and butyric acid.
Figure 11B:
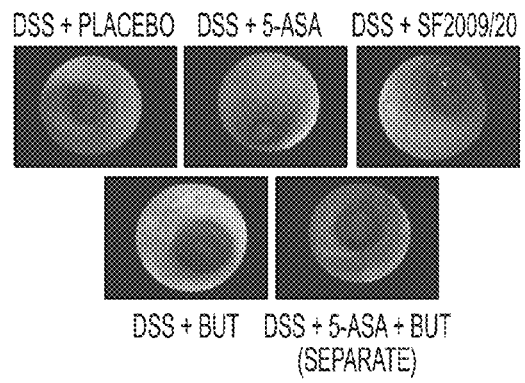
Figure 11C:
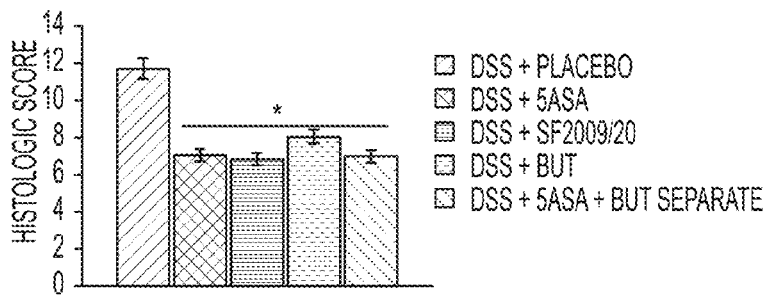
Figure 11D:
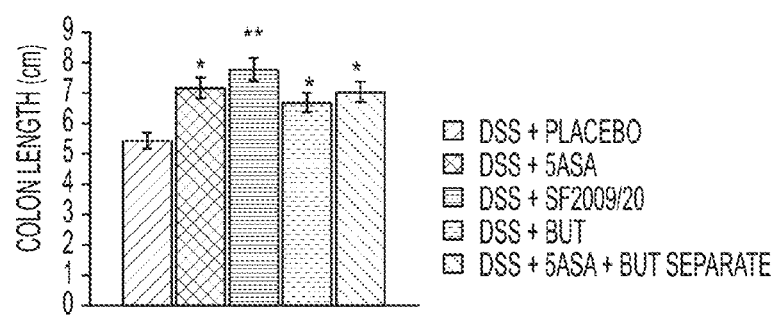
Figure 12A:
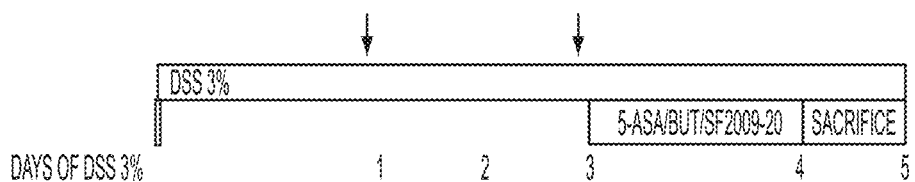
FIG. 12: Experimental results after oral administration of 200 mg/kg of 5-ASA; butyric acid; 5-ASA butyrate; placebo; 5-ASA and butyric acid.
Figure 12B:
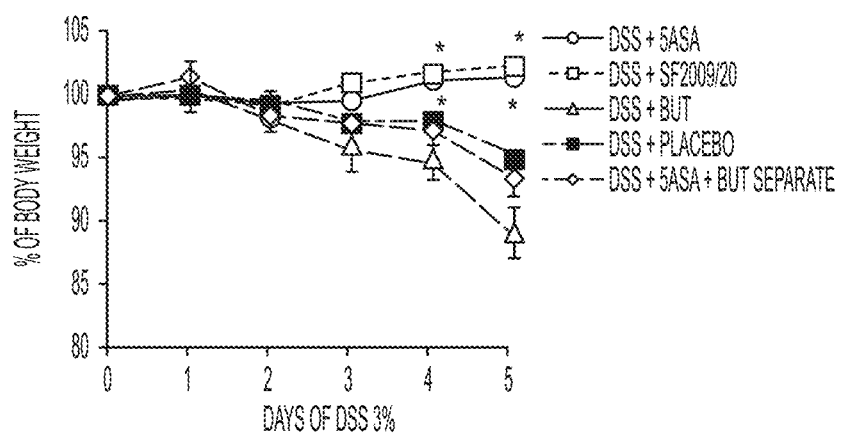
Figure 12C:
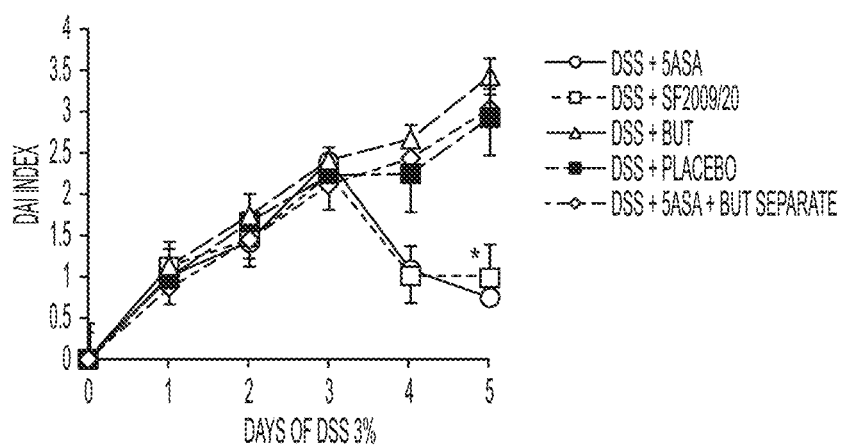
Figure 13A:
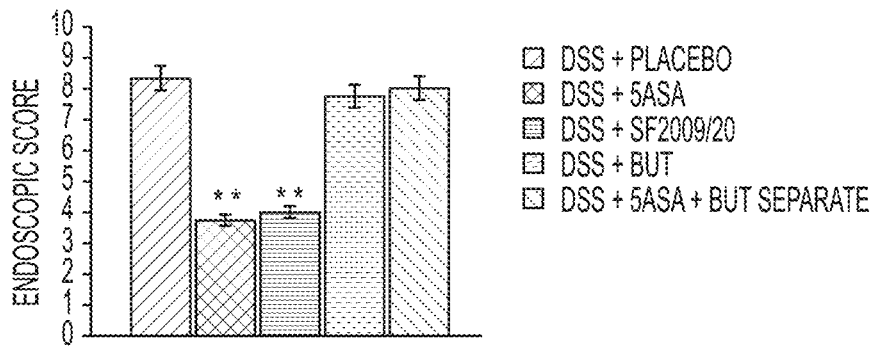
FIG. 13: Endoscopic and histological scores for experiments after oral administration of 200 mg/kg of 5-ASA; butyric acid; 5-ASA butyrate; placebo; 5-ASA and butyric acid.
Figure 13B:
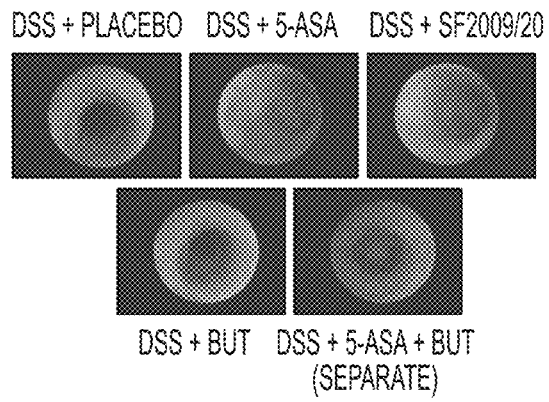
Figure 13C:
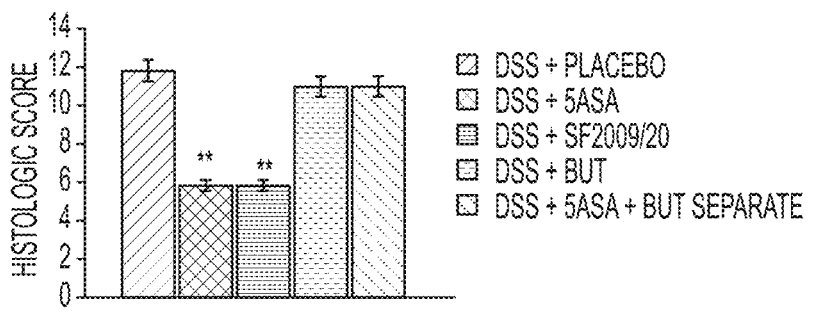
Figure 13D:
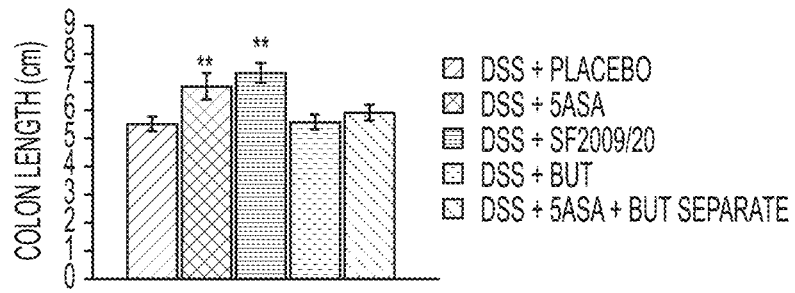

The therapeutic effect has been evaluated with different experimental procedures (a)-c)) representing either the active phase (a)) or the remission phase (b)-c)) of an intestinal inflammatory disease at different doses:

a) treatment of acute phase at 200 mg/kg/day
b) treatment of remission phase at 50 mg/kg/day
c) treatment of remission phase at 100 mg/kg/day The active phase of an intestinal inflammatory disease has been represented by the oral administration of one of the selected compounds at a dose of 200 mg/kg/day on the third day after DSS exposure and continuing for further two days (see FIGS. 12-13). The remission phase of an intestinal inflammatory disease has been represented by the oral administration of one of the selected compounds in doses of 50 (see FIGS. 8-9) and 100 mg/kg/day (see FIGS. 10-11) starting two days before DSS exposure and continuing throughout the observation period (5 days).

Results of the study can be summarized as follows:
a) 5-ASA butyrate and 5-ASA display a comparable therapeutic efficiency (low DAI, low endoscopic and histological scores).
b) 5-ASA butyrate displays a better therapeutic activity than that of 5-ASA or butyric acid if administered alone but also of the combined administration of 5-ASA and butyric acid (lower DAI, lower endoscopic and histological scores).
c) 5-ASA butyrate displays a better therapeutic activity than that of 5-ASA or butyric acid if administered alone but also of the combined administration of 5-ASA and butyric acid (lower DAI, lower endoscopic and histological scores).

These results interestingly show an improved therapeutic activity of one of the compounds of the invention (5-ASA butyrate) in particular in the remission phase of a chronic intestinal inflammatory disease, with respect to that of the combined administration of 5-ASA and butyric acid. The results therefore indicate a significant advance in the art, especially in providing an alternative compound for treating an intestinal inflammatory disease.

BIBLIOGRAPHIC REFERENCES

1. Danese S, Sans M, Spencer D M, et al. Angiogenesis blockade as a new therapeutic approach to experimental colitis. Gut 2007; 56(6):855-62.
2. Vetrano S, Borroni E M, Sarukhan A, et al. The lymphatic system controls intestinal inflammation and inflammation-associated Colon Cancer through the chemokine decoy receptor D6. Gut 2009; 59(2):197-206.
3. Axelsson L G, Landstrom E, Bylund-Fellenius A C. Experimental colitis induced by dextran sulphate sodium in mice: beneficial effects of sulphasalazine and olsalazine. Aliment Pharmacol Ther 1998; 12(9):925-34.
4. Takizawa H, Shintani N, Natsui M, et al. Activated immunocompetent cells in rat colitis mucosa induced by dextran sulfate sodium and not complete but partial suppression of colitis by FK506. Digestion 1995; 56(3):259-64.
5. Murthy S N, Cooper H S, Shim H, Shah R S, Ibrahim S A, Sedergran D J. Treatment of dextran sulfate sodium-induced murine colitis by intracolonic cyclosporin. Dig Dis Sci 1993; 38(9):1722-34.

The invention claimed is:
1. A compound of formula (I):

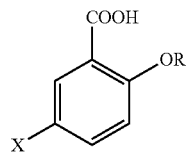

wherein:
R=$C_4$-$C_8$ alkanoyl; and
X=NH—$R_1$
where $R_1$=H, or an amine protecting group;
and/or the pharmaceutically acceptable salts thereof.
2. The compound according to claim 1, having formula (Ia):

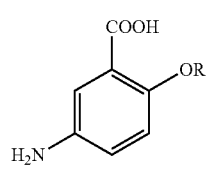

wherein:
R=$C_4$-$C_8$ alkanoyl;
and/or the pharmaceutically acceptable salts thereof.
3. 5-amino-2-(butyryloxy)benzoic acid and/or pharmaceutically acceptable salts thereof.
4. A method for treating acute or chronic intestinal inflammatory diseases, comprising the administration to a patient in need of such treatment a compound according to claim 1.
5. The method for treating according to claim 4, wherein said acute or chronic intestinal inflammatory diseases are acute intestinal inflammatory diseases.
6. The method for treating according to claim 4, wherein said acute or chronic intestinal inflammatory diseases are chronic intestinal inflammatory diseases.
7. The method for treating according to claim 6, wherein said chronic intestinal inflammatory diseases are in a remission phase.
8. The compound according to claim 2, characterised in that it is administered enterally or topically.
9. A pharmaceutical composition containing a compound according to claim 2, and at least one physiologically acceptable excipient.
10. The pharmaceutical composition according to claim 9 selected from among tablet, capsule, granule, microgranule, suspension or aqueous solution, enema, suppository, gel and rectal foam.
11. A process for the preparation of the compound of formula (Ia)

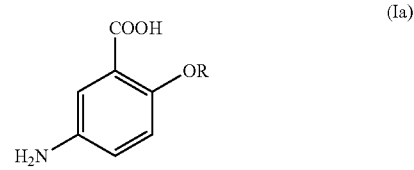 [SMILES: O=C(O)c1cc([N+](=O)[O-])ccc1O]

comprising the following steps:
a) protection of 5-ASA with an amine protecting group to obtain the compound of formula (II');

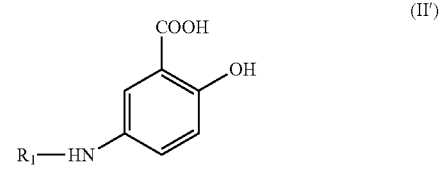

b) acylation of the hydroxyl group of the compound of formula (II') to obtain the compound of formula (III');

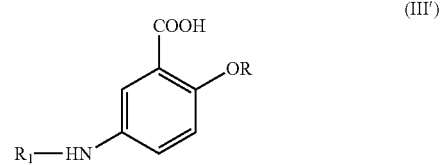

and
c) deprotection of the amino group of the compound of formula (III');
wherein:
R=$C_4$-$C_8$ alkanoyl;
and $R_1$ is an amine protecting group.

12. A process for the preparation of 5-amino-2-(butyryloxy)benzoic acid hydrochloride comprising the following steps:

a) protection of 5-ASA as a Boc-derivative to obtain the compound (II);

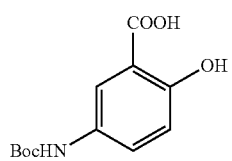
(II)

b) butyrylation of the hydroxyl group of the compound (II) to obtain the compound (III);

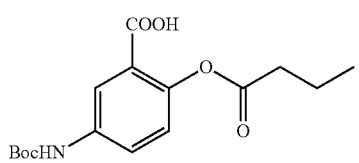
(III)

and c) deprotection of the amino group of the compound (III).

13. The process according to claim 11, wherein the step a) is conducted in an aprotic polar solvent and/or in a mixture of said solvent with $H_2O$.

14. The process according to claim 11, wherein said mixture is constituted by dioxane and $H_2O$.

15. The process according to claim 11, wherein the step a) is conducted in presence of a base in a molar ratio between 1:1 and 3:1 with respect to the 5-ASA and/or in presence of di-tert-butyl dicarbonate in a molar ratio between 1:1 and 2:1 with respect to 5-ASA.

16. The process according to claim 11, wherein the step b) is conducted in presence of a butyryl halide and/or butyric anhydride in a molar ratio between 1:1 and 3:1 with respect to the compound (II).

17. The process according to claim 11, wherein the step b) is conducted in an aprotic apolar solvent.

18. The process according to claim 11, wherein the step c) is conducted in an acid environment.

19. A process for the preparation of the compound of formula (Ia)

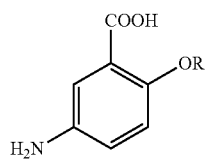
(Ia)

comprising the following steps:

a) acylation of the hydroxyl group of the compound of formula (V')

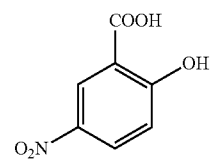
(V')

to obtain the compound of formula (VI');

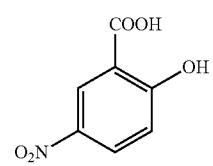
(VI')

and b) hydrogenation of the nitro group of the compound of formula (VI');

wherein:

R=$C_4$-$C_8$ alkanoyl.

20. A process for the synthesis of 5-amino-2-(butyryloxy) benzoic acid comprising the following steps:

a) butyrylation of the compound of formula (V')

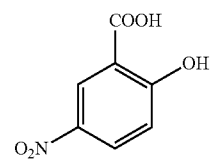
(V')

to obtain the compound (VI);

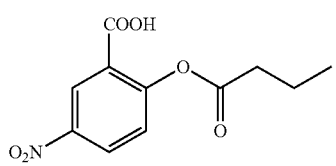 [SMILES: CCCC(=O)Oc1ccc(N)cc1C(=O)O]
(VI)

and b) hydrogenation of the compound (VI).

21. The process according to claim 19, wherein the step a) is conducted in presence of butyric anhydride and/or a butyryl halide in a molar ratio with respect to the compound (V') of between 1:1 and 5:1.

22. The process according to claim 19, wherein the step a) is conducted in presence of an acid catalysis of between 40° C. and 70° C.

23. The process according to claim 19, wherein the step a) is conducted in a polar solvent.

24. A compound of formula (Ib):

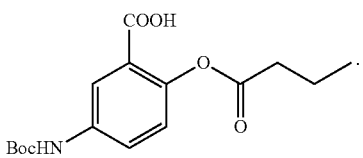

25. A process for the preparation of 5-amino-2-(butyryloxy)benzoic acid comprising deprotecting the amino group of the compound according to claim 24.

26. The compound according to claim 1, wherein the amine protecting group is the tert-butyloxycarbonyl group (Boc).

27. The 5-amino-2-(butyryloxy)benzoic acid pharmaceutically acceptable salt thereof according to claim 3, wherein the pharmaceutically acceptable salt is the hydrochloride salt.

28. The method according to claim 4, wherein the acute or chronic intestinal inflammatory diseases are selected from among IBD, IBS, ulcerative colitis and Crohn's disease and diverticular disease.

29. The method according to claim 28, wherein the acute or chronic intestinal inflammatory diseases is IBD.

30. The compound according to claim 8, wherein enterally is orally and/or rectally.

31. The compound according to claim 8, wherein topically is through anal application.

32. The process according to claim 11, wherein the amine protecting group is the tert-butyloxycarbonyl group (Boc).

33. The process according to claim 13, wherein mixture of the aprotic polar solvent and $H_2O$ is in a molar ratio between 1:1 and 3:1.

34. The process according to claim 33, wherein the molar ratio of the aprotic polar solvent and $H_2O$ is 2:1.

35. The process according to claim 14, wherein said mixture of dioxane and $H_2O$ is in a 2:1 molar ratio.

36. The process according to claim 15, wherein the molar ratio of the base with respect to 5-ASA is 1.5:1.

37. The process according to claim 15, wherein the molar ratio of the di-tert-butyl dicarbonate with respect to 5-ASA is 1.5:1.

38. The process according to claim 15, wherein the base is an organic base.

39. The process according to claim 38, wherein organic base is trimethylamine.

40. The process according to claim 16, wherein the molar ratio is 2:1.

41. The process according to claim 16, wherein the butyryl halide is butyryl chloride.

42. The process according to claim 17, wherein the aprotic apolar solvent is selected from among an aliphatic or aromatic hydrocarbon, halogenated aliphatic hydrocarbon.

43. The process according to claim 42, wherein the aprotic apolar solvent is dichloromethane.

44. The process according to claim 17, wherein the base is an organic base.

45. The process according to claim 44, wherein the organic base is diisopropylethylamine.

46. The process according to claim 17, wherein the base is in a 3:1 molar ratio with respect to the compound (II).

47. The process according to claim 18, wherein the acid environment is generated by HCl in an aprotic solvent.

48. The process according to claim 47, wherein the acid environment is generated by HCl in dioxane or HCl in ethyl ether.

49. The process of claim 11,
wherein the amine protecting group is the tert-butyloxycarbonyl group (Boc);
wherein step a) is conducted in a mixture of dioxane and $H_2O$ in a molar ratio of 2:1;
wherein step a) is conducted in presence of triethylamine in a molar ratio of 1.5:1 with respect to the 5-ASA and/or in presence of di-tert-butyl dicarbonate in a molar ratio of 1.5:1 with respect to 5-ASA;
wherein step b) is conducted in presence of butyryl chloride and/or butyric anhydride in a molar ratio of 2:1 with respect to the compound (II);
wherein step b) is conducted in dichloromethane in presence of a diisopropylethylamine in a 3:1 molar ratio with respect to the compound (II); and
wherein step c) is conducted in an acid environment generated by HCl in dioxane or HCl in ethyl ether.

50. The process according to claim 21, wherein the molar ratio is 3:1.

51. The process according to claim 21, wherein step a) is conducted in presence of butyric anhydride.

52. The process according to claim 50, wherein step a) is conducted in presence of butyric anhydride.

53. The process according to claim 22, wherein step a) is conducted in presence of sulfuric acid.

54. The process according to claim 22, wherein the temperature is about 55° C.

55. The process according to claim 53, wherein the temperature is about 55° C.

56. The process according to claim 23, wherein the polar solvent is a $C_1$-$C_4$ alcohol, dioxane, tetrahydrofuran and/or mixtures thereof.

57. The process according to claim 56, wherein the polar solvent is ethanol.

58. The process of claim 19,
wherein step a) is conducted in presence of butyric anhydride and the molar ratio is 3:1;
wherein step a) is conducted in presence of sulfuric acid and the temperature is about 55°; and
wherein the polar solvent is ethanol.

* * * * *